Figure 1:
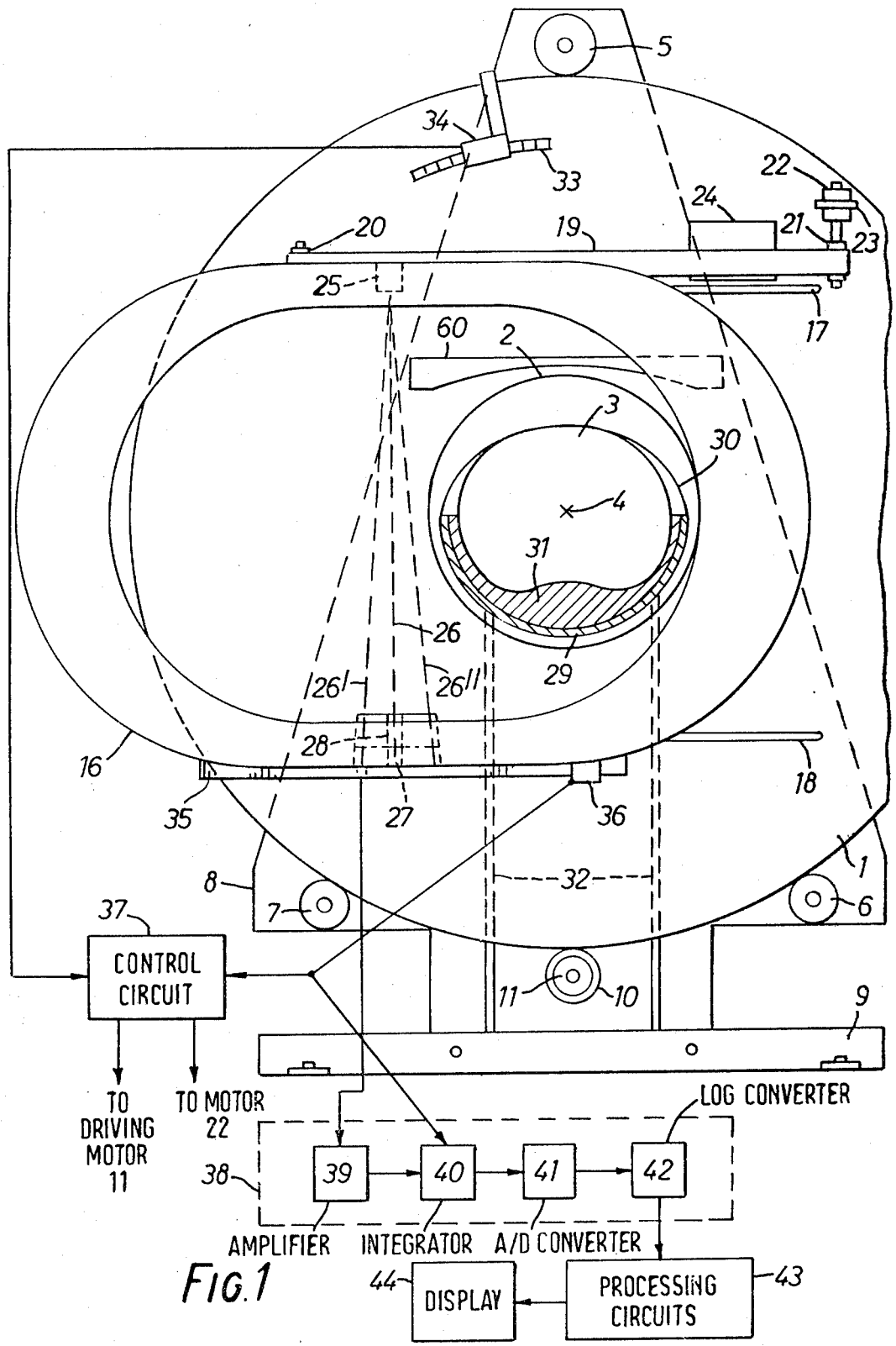

United States Patent [19]

Hounsfield et al.

[11] 4,223,384
[45] Sep. 16, 1980

[54] RADIOGRAPHY

[75] Inventors: Godfrey N. Hounsfield, Newark; MacArthur J. Gollifer, Stoke Poges, both of England

[73] Assignee: EMI Limited, Hayes, England

[21] Appl. No.: 811,281

[22] Filed: Jun. 29, 1977

[30] Foreign Application Priority Data

Jul. 1, 1976 [GB] United Kingdom ............... 27533/76

[51] Int. Cl.² ............................................. G01N 23/02
[52] U.S. Cl. ................................ 364/414; 250/358 R; 250/445 T
[58] Field of Search ............................... 364/414, 571; 250/358 R, 360, 363 R, 363 S, 445 R, 445 T, 460; 358/110, 111, 160

[56] References Cited

U.S. PATENT DOCUMENTS

| | | | |
|---|---|---|---|
| 3,809,904 | 5/1974 | Clarke et al. | 250/358 |
| 3,832,551 | 8/1974 | Bartlett et al. | 250/358 |
| 3,878,373 | 4/1975 | Blum | 364/414 |
| 3,944,830 | 3/1976 | Dissing | 250/358 R |
| 4,063,074 | 12/1977 | Wagner | 364/414 |
| 4,069,422 | 1/1978 | Hounsfield | 250/360 |

*Primary Examiner*—Errol A. Krass
*Attorney, Agent, or Firm*—Cooper, Dunham, Clark, Griffin & Moran

[57] ABSTRACT

In a computerised tomographic (CAT) X-ray apparatus passage of the radiation through high absorption (bone) regions can change a characteristic of the radiation, such as its frequency spectrum. This can introduce error into the final representation. Correction is provided by computing a first representation, identifying areas of bone and then determining corrections for those areas which can be used to provide a subsequent move accurate representation. Errors caused by scattering can also be compensated in this way.

14 Claims, 5 Drawing Figures

RADIOGRAPHY

The present invention relates to medical radiographic apparatus of the type sometimes referred to as Computerised Axial Tomography (CAT) scanners.

In CAT scanners, such as that described in U.S. Pat. No. 3,778,614, penetrating radiation, for example X-radiation, travels in a slice of a patient being examined. A source of the radiation orbits about the patient and projects the radiation in a plurality of different directions angularly distributed in the slice. The intensity of radiation emerging from the slice is then measured along each of a plurality of narrow beam paths. For the purposes of examining the patient, at least a part of the slice is designated as a matrix of elemental areas, for each of which an estimate of the absorption of the radiation is to be obtained. The narrow beam paths are then distributed so that each elemental area is intersected by a suitably large number of them. The intensity measurement obtained for each path is then representative of the total absorption suffered by radiation in passing through all the elemental areas intersected by the path. The path, in practice, intersects only part of some elemental areas and due allowance is made for this.

The intensity measurements are then process, for example as described in the said United States or in U.S. Pat. No. 3,924,129 to generate a picture in which each picture element (or elemental area of the picture) has a brightness corresponding to the absorption of radiation in the correspondingly positioned elemental area of the region. The said patents are hereby incorporated herein by reference.

One source of error in this process results from the fact that absorption is not uniform for radiation of different energies. Thus low energy radiation is preferentially absorbed leading to "hardening" of the radiation. For tissue having relatively low absorption this effect may not be significant. However for high absorption material, such as bone, the hardening is significant, leading to erroneous intensity measurements for other elemental areas on the respective paths.

It is an object of this invention to provide an arrangement for correcting for such hardness errors.

It is an alternative object of the invention to provide an arrangement for correcting for errors due to scattering of radiation in the patients body.

According to the invention there is provided a method of correcting for errors introduced into a representation of absorption of radiation, in elements of a region of a patients body, derived from measurements of absorption of the radiation along a plurality of paths passing therethrough at a plurality of angles, where the errors result from changes in the radiation as a result of passage through different absorption regions thereof, including the steps of:

(a) determining a first estimate, of the representation, susceptible to errors, (b) determining the position of regions of absorption differing from a reference level by more than a predetermined amount, (c) determining correction factors for the said changes of character in each of the paths passing through each of said determined region, and (d) correcting the absorption values for the said elements by said factors.

According to one aspect of the invention the said changes of character are changes in the energy distribution of said radiation.

According to a further aspect of the invention the said changes result from the loss of radiation introduced into a respective beam path by scattering from other regions of the body.

Figure 2:
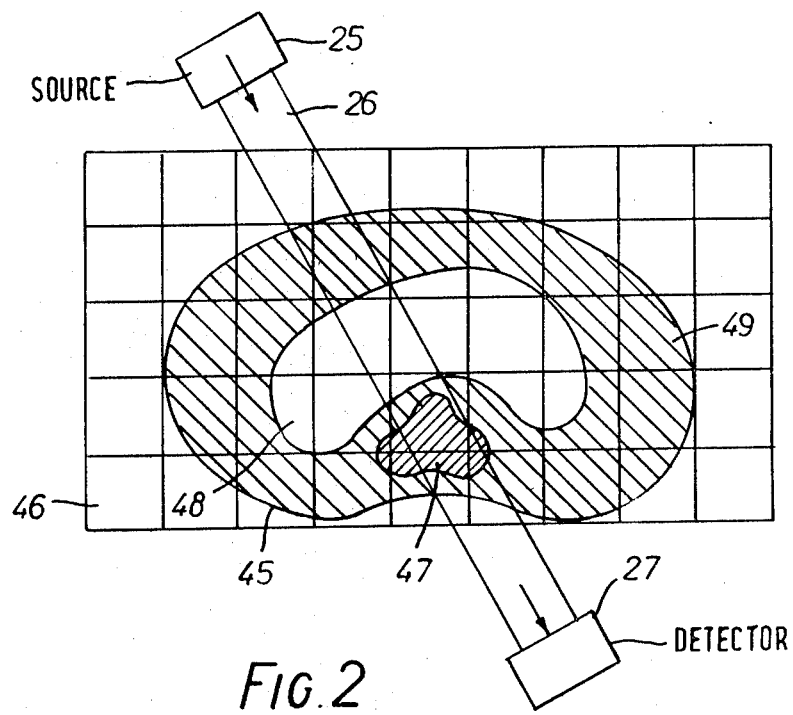
Figure 3:
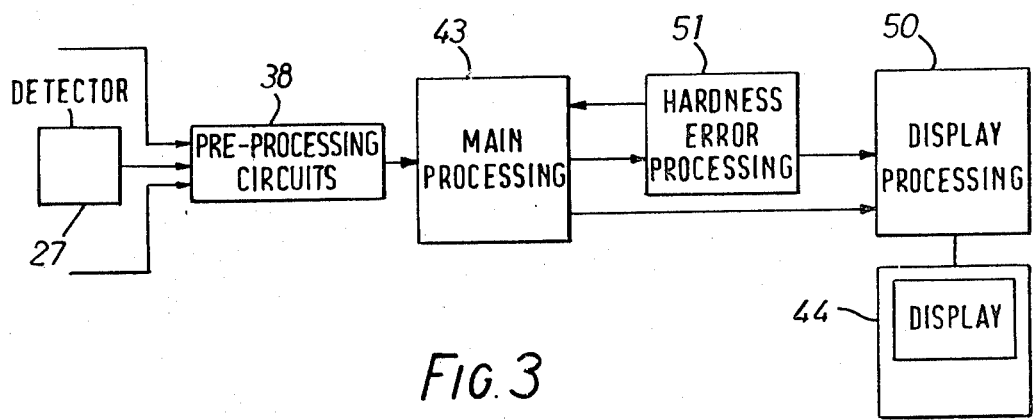
Figure 4:
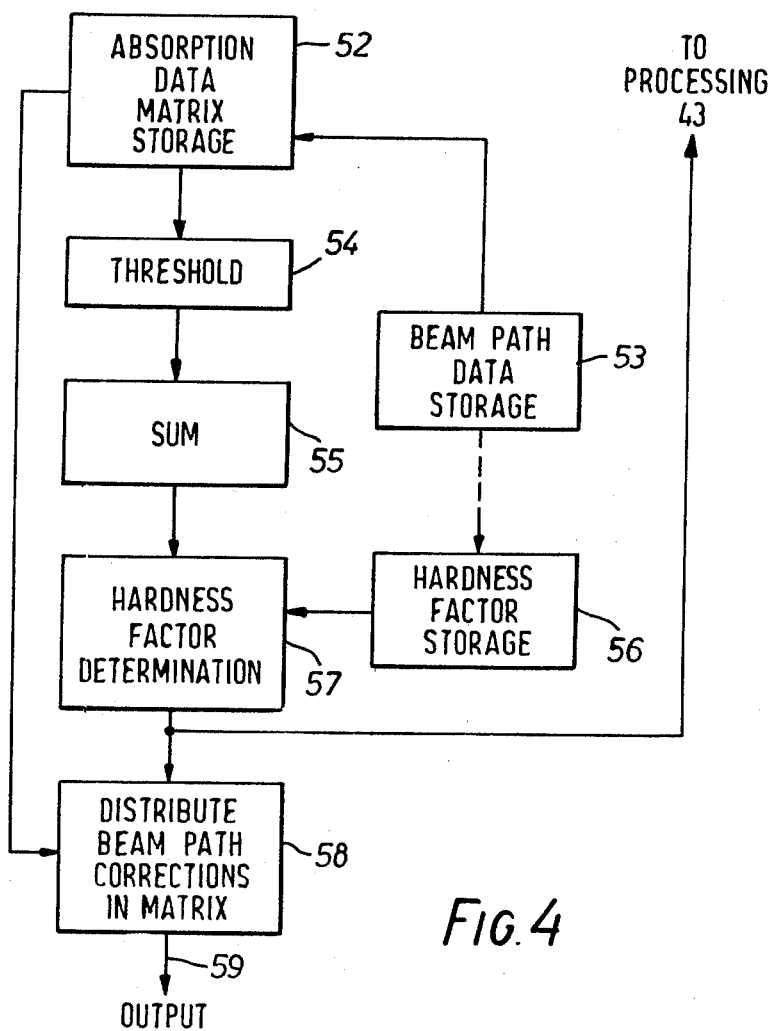
Figure 5:
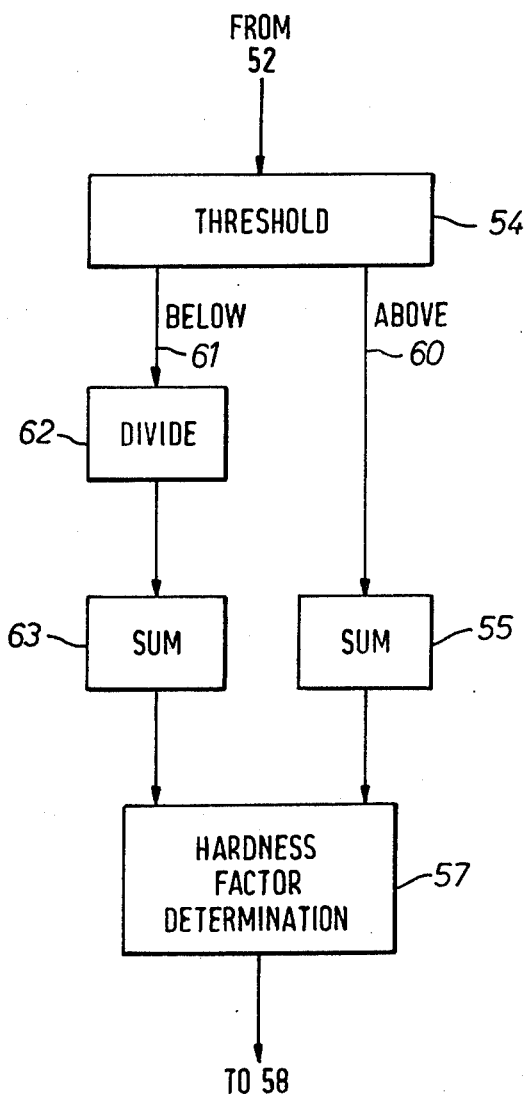

In order that the invention may be clearly understood and readily carried into effect an example thereof will now be described with reference to the accompanying drawings of which, FIG. 1 shows a radiographic apparatus suitable for use with the present invention, FIG. 2 illustrates the principle of the invention, FIG. 3 illustrates in block diagrammatic circuit form a radiographic processing arrangement incorporating the invention FIG. 4 is a flow diagram illustrating one sequence of operation for implementing the invention and FIG. 5 is an alternative for part of the diagram of FIG. 4.

Referring now to FIG. 1, the apparatus shown therein is similar in principle to the apparatus described in the aforementioned United States specification. A turntable member 1 having a central aperture 2, to accommodate a body 3 which is to be examined, is mounted vertically for rotation about an axis 4. Axis 4 is disposed centrally in the aperture 2. The member 1 is supported on three rotatable bearings 5, 6 and 7 which are journalled in the main frame 8 of the apparatus. The frame 8 remains stationary, being rigidly secured to a pedestal 9, and can take any suitable form, although it must of course be formed with an aperture coincident with the aperture 2.

The member 1 can be rotated in angular steps, as will be described hereinafter by means of a cog wheel 10 cooperating with gear teeth, not shown, cut into the periphery of the member 1. Cog wheel 10 is driven by a motor 11 which is fixed to main frame 8. If desired the gear teeth may take the form of slots so that the arrangement takes the form of a so called "Geneva mechanism" with cog wheel 10 being replaced by a rotating peg such as is used with that mechanism.

Mounted on the turntable 1, and capable of performing a reciprocating lateral scanning motion relative thereto, is a lightweight but rigid scanning yoke 16. Yoke 16 can run on linear runners 17 and 18 which are fixedly mounted on the rotatable member 1 and are disposed chordally thereof. The lateral scanning motion is imparted to the yoke 16 by virtue of a toothed belt 19, which is stretched between a pair of toothed rollers 20 and 21 journalled in respective brackets, not shown, secured to the member 1. Yoke 16 is attached to belt 19 by means of a bracket, not shown. The roller 20 is merely an idler roller, but roller 21 is driven by a reciprocating motor 22 which is attached by a strap-like bracket 23 to the member 1.

A counter-balance weight 24 is secured to the opposite run, of belt 19, to the yoke 16 and thus moves in opposition thereto to compensate for out-of-balance forces which would otherwise be set up by the lateral scanning motion of the yoke 16 and certain equipment mounted thereon, which will now be described.

Attached to the yoke 16 is a source 25 of a beam 26 of penetrating radiation, in this example X-radiation. On the opposite side of yoke 16, with respect to the aperture 2, to the source 25 is a detector 27 sensitive to the radiation generated by the source 25 and viewing the source through a collimator 28.

The body 3 is supported on a semicylindrical, one part bed 29 and is secured thereon by means of straps such as 30. Gaps between the body and the bed are filled with a suitable packing material 31 which is preferably of dough like consistency and absorbs the X-radiation to substantially the same extent as does human tissue. The material 31 is preferably contained in one or more plastic bags. The bed 29 is supported by legs 32 which stand on the pedestal 9.

For efficient operation the rotational scanning motion, imparted by the cog wheel 10 to the member 1, should be synchronised with the lateral scanning motion imparted to the yoke 16 by the reciprocating motor 22. To this end the member 1 is formed with an annular graticule, part of which is shown at 33, and a fixed photodetector 34 which with a light source, not shown, is mounted on main fram 8. Photodetector 34 provides timing pulses indicative of the passage past it of markings on the graticule 33. Thus the rotational scanning motion of member 1 is monitored. Similarly a linear graticule 35 is fixedly attached to the yoke 16 and cooperates with a second photodetector 36, which is mounted on the member 1 so as to rotate therewith, and a similarly mounted light source, not shown, to produce timing pulses indicative of the progress of the lateral scanning. Both graticules 33 and 35 comprise translucent or transparent members bearing opaque lines printed, etched or otherwise provided thereon. The two sets of timing pulses are fed to a control circuit 37 which controls the motor 22 and the motor 11 in such a way that, after each step of rotational motion, a single lateral scan is carried out to traverse the source 25 and the detector 27 in one direction or the other across the aperture 2. Thus a single lateral scan is carried out for each dwell angle of the member 1.

The detector 27 is, for example a scintillator crystal, such as sodium iodide, with an associated photomultiplier tube, or a photodiode, and thus provides electrical signals indicative of the amount of radiation detected thereby. The electrical signals so provided are applied to a pre-processing circuit 38, which contains an amplifier 39, a resettable integrator 40, an analogue-to-digital converter 41 and a logarithmic converter 42. The integrator 39 to read and reset synchronously and periodically by means of timing pulses derived from the photodetector 36; the arrangement in this example being such that the reading and re-setting occurs some one hundred and sixty times during each lateral scan in either direction to provide data for a set of parallel beam paths across the body. After one lateral scan the member 1 is rotated through a predetermined angle and a second lateral scan provides data for a further set of parallel paths. The process is repeated until sufficient such sets have been provided over about 180° and all of the output signals obtained during the scanning are processed in a processing circuit 43 to evaluate the absorption coefficient, with respect to the radiation used, at a plurality of locations distributed over the slice of the body 3 which lies in the plane of the beam of X-rays generated by the source 25. The distribution of absorption coefficients thus derived is then displayed on a display unit 44.

Preferably the processing is carried out in accordance with the technique described and claimed in U.S. Pat. No. 3,924,129. This technique involves a form of convolution for which the output signals are assembled in sets relating to sets of paths, preferably parallel, through the body. Each output signal is then modified by combining it with weighted components of other output signals of its own set; the weighting being in accordance with a function which is negative, and decreases in amplitude as the distance from the path giving rise to the output signal being modified increases. The modified output signals are then additively combined in accordance with a layergramming procedure; the modification of the output signals being such as to compensate for the known inaccuracies of conventional layergrams. In relation to a predetermined elemental area (in fact a small volume) in the slice being examined the arrangement is such that the modified absorption values for all beam paths passing through, or near to, that elemental area are combined to give an absorption coefficient for the elemental area. In practice beams at the angular dispositions of all of the parallel sets of paths may not pass sufficiently close to each such evaluation area. For this reason interpolation is applied to the modified data for each parallel set of paths to obtain modified data for a new set of an increased number of such paths to ensure that at least one passes sufficiently close to each evaluation area.

FIG. 1 also shows modifications which can be made to the apparatus to operate according to an alternative arrangement, as described in U.S. Pat. No. 3,946,234. In such an arrangement source 25 is arranged to provide the radiation as a planar, fan-shaped distribution between limits 26' and 26". The detector 27 is replaced with an array of detectors, typically thirty, cooperating with respective collimators to define a corresponding number of beams in the fan distribution. In one example the neighbouring collimators are inclined to each other at angles of $\frac{1}{3}°$. Thus the angular spread for thirty detectors is $9\frac{2}{3}°$ between the centrelines of the extreme beams. Thus, for one hundred and sixty integration intervals during a lateral scan, output signals are provided which are indicative of the absorption suffered by the radiation on traversing thirty sets of parallel paths, each set displaced by $\frac{1}{3}°$ from its neighbour. The rotation at the end of each lateral scan is then by the ten degrees of the fan distribution. For processing an individual circuit 38 is provided for each detector channel, to provide data to processing circuits 43.

Although the apparatus described in relation to FIG. 1 is essentially that described in the said U.S. Pat. No. 3,778,614 and U.S. Pat. No. 3,924,129, or, with the appropriate changes, the alternative version of U.S. Pat. No. 3,946,234, it will be understood that the invention to be described can be applied to other forms of apparatus providing absorption data of the same nature.

For the purposes of explanation there is shown in FIG. 2 a simplified section of a slice 45, of the patient's body 3, on which is shown a designated matrix of elemental areas such as 46. In this example forty five elements of the matrix are shown, extending beyond the slice. It should be understood that this example is chosen for clarity of illustration and in practice the matrix would comprise a much larger number of elements, typically greater than 100,000 and that they may lie in only a restricted region of such a slice. Also for the purposes of clarity the section of the body will be assumed to include only a region 47 of bone, a region 48 of air and other regions 49 of intermediate density. However in practice it would be considerably more complex.

The beam 26 of radiation projected from source 25, is arranged to be incident on detector 27. The output signal representing the intensity of the radiation collected at detector 27 is related to the absorption along path 26. The signal, which will be called an "edge reading" is used together with similar absorption values for many other paths at many angles, to determine absorption coefficients for all elements, such as 46.

Considering beam path 26, however, it will be seen that it passes through, in sequence, intermediate region 49, air 48, more of intermediate region 49, bone 47 and further intermediate region 49. The bone 47 causes the hardness of the radiation to change, rendering the absorption reading to be in error in respect to regions 47, 48 and 49.

In applying the correction of the present invention, all edge readings obtained by detectors such as 27 at all positions of source 25 are processed by an appropriate method to obtain a first estimate of absorption values for the matrix of elements. Although these actual values are probably not entirely correct due to bone error, they are in approximately correct proportion so that the existence of regions of bone such as 47 can be seen therefrom. Taking beams such as 26 it is clearly possible to determine the extent of bone 47 through which beam 26 passed. This may be achieved by manual means but is preferably performed in a computer using, for example, known pattern recognition techniques. The calculation need only be approximate to yield at least an estimate of a correction. It can readily be known, either from calculation or previous measurement, how much hardening is obtained from any proportion of bone so that the edge reading of detector 26 can be corrected appropriately. The entire CAT picture may then be redetermined using such corrected edge readings.

However, in a simpler preferred embodiment, the correction factor is applied not to the edge reading but to the first calculated absorption values for elemental areas intercepted by beam 26 in proportion to their degree of interception thereby.

It will be understood that the correction is applied to elemental areas intercepted by the beam 26 both before and after passage through bone 47. This is because the error is the same whether it is caused by an unexpected change of hardness of radiation already including absorption information from an elemental area or about to be used to obtain such information. In either case the effect at detector 27 cannot be distinguished.

There is shown in FIG. 3 a simplified block diagram of the processing for obtaining the final picture. The edge readings from the detectors such as 27 are first applied to the pre-processing circuits indicated generally at 38. The data are then processed, as referred to hereinbefore, in processing circuits 43 to achieve a first estimate of a picture. This estimate can if desired be provided directly to display processing 50, comprising, for example, standards conversion, for display on the display unit 44. The picture is also provided to hardness error processing circuits 51 together with data indicating the orientations of beam paths in the body region being examined. Circuits 51 determine the required hardness correction factors and either return appropriately corrected edge readings to circuits 10 for reprocessing or provide corrected values for each matrix element to display processing 50. It will be understood that many detailed arrangements may be provided for calculating the hardness correction, according to the principles explained hereinbefore. Such arrangements may comprise specially constructed circuits or may use an appropriately programmed digital computer. In the latter case processing circuits 43 and 51 may conveniently be provided by a single computer. The implementation of a computer program to apply the correction factors of the invention may readily be achieved by those skilled in computer programming. However, for clarification of the required procedure for processing in circuits 51 FIG. 4 shows a block diagrammatic circuit. It should be understood that this schematic Figure does not represent a detailed arrangement of circuits but is more of the form of a flow diagram for a program. Of course a special purpose circuit could take a similar form.

Turning to FIG. 4 the calculated absorption values are held in storage 52 in locations corresponding to their positions in the matrix. Further storage 53 holds data, in the form of stored co-ordinates for the matrix, representing the paths followed through the elemental areas by each beam for which an edge reading has been obtained. Clearly these beam paths can be the same for each examination and can be determined in advance as part of a setting up procedure for the equipment. Alternatively they can be calculated as required using data from photo detectors 34 and 36.

The beam path co-ordinates are provided to matrix storage 52 where values for all elements along a beam path are withdrawn progressively. In doing this it must be remembered that the beam path may only intersect a proportion of each element and that only a corresponding proporation of the respective correction factor should be added into the sum. The procedure is essentially the same as that described in U.S. Pat. No. 3,778,614 for summing absorption values along a beam path and may be carried out in the same manner. They are then subjected to a threshold 54 to identify individual absorption values which exceed a predetermined absorption level, i.e. those which represent bone. The data for elements of each beam path, after threshold indentification, are summed in summer 55 to provide high absorption beam path data signals which relate only to absorption of the radiation by elements above the threshold. These data signals represent the extent to which the radiation of the respective beam has been subject to absorption which will cause a hardness error.

There are also held in storage at 56 precalculated or premeasured hardness factors representative of hardness changes introduced by bone of different absorption levels. These may be determined by measurement from a phantom body of known absorption. There is a factor for each of a plurality of ranges of values of the high absorption beam path data. These are withdrawn from storage in response to a level analysis at 57 of the beam path data from 55 to provide a hardness correction factor for each beam path.

The correction factor for each beam path is then provided to processing circuits 43 to be multiplied by, or added to as desired, the edge reading for the same path. The edge readings as corrected are then reprocessed to give a more accurate representation for display or for recalculation of hardness errors in a further cycle of correction.

Alternatively the hardness corrections for each beam path may be used directly to correct each element of the first estimate of the representation in matrix store 52. The representation from store 52 is provided to unit 58 in which the correction for each beam path is used, in appropriate proportions to correct the value to each element intersected or part intersected by that path. As before the correct proportioning can be achieved as described in U.S. Pat. No. 3,778,614. The corrected representation is then output directly at 59 for display.

In practice such correction takes a finite, though short, time. It may, therefore, be desirable to display the uncorrected matrix representation from store 52 while a correct version is being evaluated. This first displayed picture can then be updated or replaced by the corrected picture when available.

Although the correction described is for hardness errors introduced by dense material such as bone, it should be noted that lesser errors are introduced by regions of intermediate density. Such lesser errors may be ignored but if desired they may also be corrected in the same manner as the bone but with appropriate correction factors. A desired procedure is to use an intermediate absorption value as a reference, to apply one correction to values above that level say by more than a predetermined amount and an opposing correction to values below that level by a similar amount. That means in effect applying a negative correction to values such as those which have an absorption significantly less than tissue.

One means of achieving this is shown in FIG. 5 which is a modification of part of the circuit of FIG. 4. The threshold 54 provides, at 60, values above the preset level and, at 61, values below a lower level. If desired a single intermediate threshold level may be used. The values below the level, which may represent, say, regions of air in the body, are divided at 62 by a factor to reduce their significance compared with the high or bone corrections. The factor may be determined empirically but a typical value is 100. They are also summed, at 63, to provide low absorption beam path data which are also provided to circuits 57 at which their respective correction factors are determined. The corrections for the low absorption beam path data are opposite in sign to the high absorption data but are otherwise utilised in the same manner.

In some examples of the apparatus, such as that described in U.S. Pat. No. 3,946,234, it is known to include in the path of the X-rays saddle-shaped absorbing members. One typical such member is shown in FIG. 1 at 60. The saddle shaped members, which may be disposed on both sides or only on one side of the body, serve to correct the absorbing path length of the body for variations caused by its substantially circular cross-section.

Members such as 60 also, however, introduce changes in hardness of the radiation in view of the material, typically aluminium, from which they are made. A method of compensating for errors introduced by these members has been described in U.S. Pat. No. 4,028,554. However it will be apparent that such correction may be advantageously combined with the corrections of the present invention by holding in store 54 additional factors calculated for member 60 and applying them with the tissue error factors. Preferably the corrections for members 60 should be applied to the edge readings after they have been corrected for tissue hardness errors.

Since the corrections calculated for member 60 can be precalculated, it is advantageous to combine them with the tissue error factors as stored in storage 56. This is to say each beam path data signal from 55 (or 63) is allocated a correction factor not only on the basis of its amplitude but also on the basis of the position at which it intercepted 60, represented by its distance from the centre, and therefore the thickness of material through which it passed.

The beam path data storage 53, when initiating a beam path data signal from 52 also indicates to storage 56, as shown by the broken line path, what the orientation of the next beam is. The orientation, which is predetermined when the apparatus is set up, has allocated to it a particular set of hardness factors for a beam in that position. One of these is then selected for the respective data signal on the basis of its amplitude. As mentioned hereinbefore, and as described in U.S. Pat. No. 4,028,554, it is convenient to determine the respective factors by measurement using a phantom body.

It should be noted that hardness errors are not the only way in which the material of the body introduces errors into the readings. It is known that radiation is scattered from absorbing regions of the body so that not all data entering the detector 27 has travelled directly along path 26 from the source 25. In practice, for a body of fairly uniform absorption, scattering is uniform and each detector position results in a similar scattered radiation input therefore giving, on balance, little error in the final picture. However high absorption regions such as bone upset this general balance by shielding a detector and reducing its scatter input below the mean. The effect is that of a change of character similar to that produced by the hardness error and may be corrected in the same way. It is necessary to compute or measure an average scatter level and, knowing the approximate absorption of bone in each path such as 26, to uprate the appropriate edge reading by a factor accounting for the loss of scattered radiation.

Although the invention has been described in terms of particular scanning arrangement it should be understood that the error correction is not specific to the scanning by which the data was obtained.

What we claim is:

1. A method of correcting for errors introduced into a representation, of the distribution of absorption of radiation in a region of a patient's body, derived from measurements of the radiation transmitted through the region along a plurality of paths passing therethrough at a plurality of angles, where the errors result from changes in the energy spectrum of the radiation, the method including the steps of:

(a) using the radiation measurements to determine a first estimate of the representation in the form of estimates of the absorption of the radiation in individual elements of a matrix of elements notionally defined in the region,
    (b) determining from the first estimate the positions in the region of specific elements having absorption which differs from a reference level by more than a predetermined amount,
    (c) deriving for each of the radiation paths, corrections for said changes in the energy spectrum of the radiation caused by those specific elements which intercept the respective path, at least in part, and
    (d) using said corrections to revise the estimates of absorption for all elements intercepting the respective direction, at least in part.

2. A method according to claim 1 in which the specific elements determined from the first estimate are those for which the absorption exceeds the reference level by the predetermined amount.

3. A method according to claim 1 in which the specific elements determined from the first estimate are those for which the absorption exceeds the reference level by a predetermined amount and those for which the absorption is exceeded by the reference level by a predetermined amount.

4. A method according to claim 3 in which the absorptions for specific elements exceeded by the reference level are divided by a predetermined factor prior to determination of the corrections.

5. A method according to claim 1 in which the estimated absorptions are revised by correcting the radiation measurements for each path by the correction determined for the path and deriving a new representation from the corrected radiation measurements.

6. A method according to claim 5 in which the radiation measurements are corrected by multiplication by the corrections for the respective paths.

7. A method according to claim 1 in which the estimated absorptions are revised by applying to each estimated absorption a proportion of the correction for each path intercepting the respective element.

8. A method according to claim 7 in which the estimated absorptions are revised by multiplication by the respective proportion.

9. A method according to claim 1 including the step of correcting for changes, in the energy spectrum, introduced external to the body.

10. A method according to claim 9 in which the changes introduced external to the body result from members arranged to approximately equalize absorption across the body to provide an approximately circular cross-section thereof.

11. An apparatus for determining a representation of the absorption of penetrating radiation in a region of the body of a patient, the apparatus including: means providing a plurality of absorption data signals, each representing the absorption suffered by radiation in passing through the region along a respective one of a plurality of beam paths; means for processing the absorption data signals to provide absorption coefficients for individual elements of a matrix of elements defined in the region; means for identifying elements of the matrix for which the absorption values are within one or more predetermined ranges; means for reconstructing absorption data signals for said paths to represent the absorption suffered by the radiation in passing through said elements having absorption in said ranges; means for determining, from the respective reconstructed absorption data signals, correction absorption data signals, for each beam path, representing changes required to the original absorption data signals to correct for errors introduced by changes in the energy distribution of the radiation resulting from elements through which the beam path has passed; and means for using the so corrected absorption data signals to provide absorption coefficients for said elements corrected for said errors resulting from said changes.

12. An apparatus according to claim 11 in which changes of character are changes in the frequency spectrum of the radiation resulting from passage through said elements.

13. A method for constructing a representation of the distribution of attenuation of penetrating radiation in a region of the body of a patient, the method including:
(a) generating penetrating radiation directed at the region and propagating therethrough along a plurality of paths at a plurality of dispositions and measuring the intensity of the radiation after transmission therethrough,
(b) determining from the radiation measurements first estimates of attenuation coefficients, for the radiation, of individual elements of a matrix of elements notionally defined in said region,
(c) determining from said first estimates the positions in the region of specific elements for which the estimated attenuation coefficients differ from a predetermined level in a predetermined manner,
(d) evaluating, for said paths through the region, corrections each of which is related to the attenuation coefficients of those specific elements which intersect the respective path at least in part, and
(e) using said corrections to provide second estimates of the attenuation coefficients, for the radiation, of said individual elements, for which errors, resulting from the effects of said individual elements, are reduced.

14. A medical diagnostic X-ray machine, for examining a slice of a patient which extends along a substantially planar section through the patient, comprising
means for supporting the patient;
means for generating X-radiation directed at the patient and propagating substantially along said section from each of a number of locations distributed along an orbit around the patient and means for detecting the X-radiation after passage through the patient along each of a number of directions at least some of which are at an angle to each other, and for producing output signals each related to the amount of radiation which has passed through the patient along a respective one of said directions;
means for forming from said output signals first picture element signals each of which represents a first estimate of the X-ray response of a respective one only of the elements of a finite Cartesian matrix notionally superimposed on the patient slice or a portion thereof;
means for providing a reference level signal and means for determining the position in the slice of slice elements having X-ray response differing from the reference level signal in a predetermined manner;
means for deriving from said picture element signals correction factors related to estimated changes in character of the X-radiation in passing through the patient along the respective beam paths and means for causing a change in said first picture element signals based on said correction factors to derive thereby second picture element signals; and
means for displaying said second picture element signals to display thereby a picture of the anatomy of said slice of the patient examined with the machine.

* * * * *